United States Patent [19]

Weischedel

[11] Patent Number: 5,751,144
[45] Date of Patent: May 12, 1998

[54] METHOD AND DEVICE INCLUDING PRIMARY AND AUXILIARY MAGNETIC POLES FOR NONDESTRUCTIVE DETECTION OF STRUCTURAL FAULTS

[75] Inventor: Herbert R. Weischedel, South Windsor, Conn.

[73] Assignee: NDT Technologies, Incorporated, South Windsor, Conn.

[21] Appl. No.: 685,414

[22] Filed: Jul. 23, 1996

[51] Int. Cl.$^6$ ............................ G01N 27/82; G01N 27/90
[52] U.S. Cl. ........................ 324/240; 324/220; 324/232; 324/235; 324/242
[58] Field of Search .................... 324/220, 221, 324/228, 232, 235, 240–242

[56] References Cited

U.S. PATENT DOCUMENTS

| | | | |
|---|---|---|---|
| 3,845,381 | 10/1974 | Hart | 324/221 |
| 4,495,465 | 1/1985 | Tomaiuolo et al. | 324/232 |
| 4,659,991 | 4/1987 | Weischedel . | |
| 4,827,215 | 5/1989 | Van Der Walt . | |
| 4,855,676 | 8/1989 | Cecco et al. | 324/232 X |
| 5,036,277 | 7/1991 | van der Walt | 324/232 X |
| 5,128,613 | 7/1992 | Takahashi | 324/235 |
| 5,198,765 | 3/1993 | Van Der Walt . | |
| 5,237,270 | 8/1993 | Cecco et al. | 324/232 X |
| 5,293,117 | 3/1994 | Hwang | 324/232 X |
| 5,414,353 | 5/1995 | Weischedel . | |
| 5,446,382 | 8/1995 | Flora | 324/232 |

OTHER PUBLICATIONS

German article, *Die elektromagnetische Prüfung von Drahtseilen* (The electromagnetic Testing Of Wire Cable) by Urs Balthasar Meyer (1973), Mitteilungen Aus Dem Institut Für Electrische Maschinen An Der ETH published by Juris Druck+ Verlag Zurich, pp. 107–109.

*Nondestructive Testing Handbook*, vol. 4, (1986) "Electromagnetic Testing", Eddy Current, Flux Leakage and Microwave Nondestructive Testing, pp. 212–215.

Thesis—*Ein Beitrag zur magnetinduktiven Ouerschnittsmessung von Drahtseilen* (A Contribution to the Magnetic–Inductive Measurement of Wire Cable Crosssections) by Wolfgang Rieger, University of Stuttgart, (1983) pp. 49 and 98.

Primary Examiner—Gerard R. Strecker
Attorney, Agent, or Firm—McCormick, Paulding & Huber

[57] ABSTRACT

A magnetic inspection device for detecting structural faults in elongated magnetically permeable objects has two primary and opposite poles which induce a magnetic flux to place the object at least near magnetic saturation. At least one auxiliary pole is positioned on the inspection device between the primary poles and serves to change the level of the magnetic flux induced by the primary poles so as to induce eddy currents during relative movement of the inspection device and the object. At least one sensor positioned on the inspection device detects eddy current changes which are representative of structural faults.

26 Claims, 5 Drawing Sheets

METHOD AND DEVICE INCLUDING PRIMARY AND AUXILIARY MAGNETIC POLES FOR NONDESTRUCTIVE DETECTION OF STRUCTURAL FAULTS

BACKGROUND OF THE INVENTION

The present invention relates to an inspection method and device for nondestructive inspection and evaluation of magnetically permeable objects such as wire cables, rods, pipes, and the like. The invention is concerned more particularly with an electromagnetic inspection method and device for detecting structural faults in the objects.

Eddy current (EC) techniques are known for inspecting elongated magnetically permeable objects such as wire cables, rods, pipes, and the like for structural defects such as stress-corrosion cracks. For example, my U.S. Pat. No. 5,414,353, the disclosure of which is herein incorporated by reference, teaches a magnetic saturation/eddy current method and device for detecting and determining the location of structural faults along magnetically permeable objects. The device includes a magnet means which induces a magnetic flux which magnetically saturates the object along a longitudinal section. The magnet means and the induced magnetic flux move progressively and longitudinally relative to the object whereby a longitudinal section of the object experiences a changing magnetic flux which induces eddy currents. An eddy current change detecting means is provided on the magnet means and is to be positioned adjacent to the relatively moving object to detect changes in eddy currents which are representative of structural faults in the object.

Unfortunately, eddy current (EC) methods for objects made of ferromagnetic materials suffer from two critical problems. First, the high permeability of the ferromagnetic material acts as a shield because of the frequency-times-permeability-times-conductivity term that appears in skin depth calculations. Thus, full-wave penetration of the object wall is difficult to achieve. Second, the permeability, coercive force and remanence of steel are influenced by material properties, by internal stresses and by structural conditions. These magnetic characteristics depend on the selection of the initial materials and the melting, foundry, rolling and annealing processes. Because these magnetic characteristics are not well controlled during manufacture and handling of pipes, magnetic properties can vary in a random fashion along the length of the elongated object. Localized permeability variations, in the absence of auxiliary magnetization, usually lead to noise levels that prevent sufficiently high sensitivities during testing.

There are three ways to increase the through-wall penetration depth and the signal-to-noise ratio of EC inspections. First, the object can be magnetically saturated to decrease its magnetic permeability and increase skin depth. This magnetic saturation also decreases localized permeability variations, which in turn decreases distortions of the inspection signals, thereby improving the signal-to-noise ratios. Second, the skin depth can be increased by lowering the excitation frequency. And, third, the strength of the excitation signal can be increased.

For through-wall inspections, it is therefore necessary to magnetically saturate the material to be inspected by applying an ultra-low or zero frequency magnetic field (hereinafter called a DC magnetic field). When ferromagnetic material is magnetically saturated, its relative permeability approaches a value of one (i.e., that of air). When thus saturated, the material behaves like a non-ferromagnetic material and permeability variations will not affect the EC inspection. The low relative permeability decreases the background noise and improves the signal-to-noise ratio so that discontinuity signals can be sensed. In addition to noise reduction, the DC magnetization method decreases the skin effect which is otherwise problematic when applying an alternating magnetic field associated with conventional eddy current methods.

Feasibility experiments have shown that a simple DC magnetic saturation method is easily implemented. However, for a reliable through-wall detection of structural faults such as axial slits, two necessary conditions must be simultaneously satisfied. First, the magnetically permeable elongated object must be magnetically saturated or nearly-saturated. Second, substantial eddy currents must be induced so that eddy current changes representative of structural faults can be readily detected. The previous two conditions will hereinafter be referred to as the "necessary conditions".

Unfortunately, the necessary conditions are somewhat incompatible with each other because the magnet means moving relative to the tested object induces a changing magnetic field which, according to Lenz's law, excites eddy currents together with an associated magnetic field that opposes the change in the magnetic field which produced these eddy currents. Therefore, the induction of eddy currents in this self-excited eddy current (SEEC) method retards the diffusion of the magnetic flux through the object wall so as to oppose magnetic saturation of the pipe. Full magnetic saturation (or near saturation) is achieved only after the eddy currents have decayed toward zero magnitude. In other words, for a simple implementation of an SEEC method, the independent control of the magnetic saturation together with the simultaneous induction of strong SEECs is not possible. As such, prior SEEC apparatus and methods suffer from the difficulty of simultaneously achieving the necessary conditions for reliable structural fault detection.

Accordingly, it is a general object of the present invention to provide a simple method and apparatus for achieving the above-mentioned necessary conditions and for determining structural faults in a magnetically permeable elongated object. Structural faults such as longitudinal stress-corrosion cracks, hard spots, manufacturing flaws, residual stress or stress caused by bending or sagging in a pipe, and wire contact pattern changes in a wire cable caused by loose wires are more easily detected by the described method.

It is another object of the present invention to provide an eddy current/magnetic saturation method which significantly decreases background noise so as to detect structural faults with improved sensitivity.

SUMMARY OF THE INVENTION

The present invention resides in a magnetic inspection method and device for nondestructively detecting structural faults in elongated objects such as wire cables, rods, pipes, and the like.

One aspect of the present invention relates to a method for inspecting a magnetically permeable elongated object for structural faults. The method comprises the steps of inducing a static magnetic flux by means of a magnet device through a longitudinal section of a magnetically permeable elongated object for generally magnetically saturating the object. The longitudinal section extends between first and second opposite primary poles of the magnet device. The poles are magnetically oriented radially relative to the object to be tested. The static magnetic flux is changed in magnitude at a portion of the object positioned adjacent to at least one flux-changing means provided on the magnet device between the first and second primary poles. The magnet device and the induced static magnetic flux are moved progressively and longitudinally relative to the object, whereby circumaxial eddy currents and associated opposing magnetic fluxes are induced in portions of the moving object adjacent to the first primary pole and the flux-changing means. The first primary pole is positioned upstream of the flux-changing means such that at a portion of the object adjacent to the flux-changing means the eddy currents induced by the first primary pole have decayed and such portion of the object is generally at magnetic saturation. At least one signal is generated from a portion of the object downstream from the flux-changing means where combined static and opposing magnetic fluxes magnetically saturate such portion and where the eddy currents induced adjacent to the flux-changing means have not decayed such that eddy current changes representative of structural faults can be readily detected. The location and magnitude of a structural fault within the moving portion of the object are determined in response to the generated signal.

Another aspect of the present invention resides in a magnetic inspection device which comprises magnet means including first and second primary magnetic poles oppositely polarized relative to each other and spaced from one another for positioning and movement longitudinally relative to an elongated magnetically permeable object to be tested. The primary poles are polarized radially relative to the object and the first primary pole is positioned upstream of the second primary pole relative to magnet means movement. The magnet means further includes at least one auxiliary pole positioned on the magnet means between the primary poles. The auxiliary pole has the same magnetic poling as one of the primary poles. The primary poles induce a static magnetic flux through a longitudinal section of an object extending between the primary poles for generally magnetically saturating the object. The auxiliary pole changes the magnitude of the static magnetic flux in a portion of the object adjacent to the auxiliary pole. The primary poles and the auxiliary pole induce circumaxial eddy currents and associated opposing magnetic fluxes in moving portions of the object adjacent to the first primary pole and the auxiliary pole. The auxiliary pole is located sufficiently downstream of the first primary pole such that at a portion of the object adjacent to the auxiliary pole the eddy currents generated by the first primary pole have decayed and such portion of the object is generally at magnetic saturation. At least one eddy current change detecting means is positioned downstream from the auxiliary pole such that the detecting means is adjacent to a portion of the relatively moving object where combined static and opposing magnetic fluxes magnetically saturate such portion and where eddy currents induced by the auxiliary pole have not decayed such that eddy current changes representative of structural faults generate at least one readily detectable signal in the eddy current change detecting means. The auxiliary pole and the eddy current change detecting means are preferably supported in a housing or module that is located between the primary poles such that the auxiliary pole and eddy current change detecting means are close to and in fixed position relative to each other. A digital processor is provided for determining the location and magnitude of a structural fault within the moving portion of the object in response to the signal.

BRIEF DESCRIPTION OF THE DRAWINGS

FIG. 1b is a graph illustrating magnetic flux induced in the section of the object by the inspection device of FIG. 1a.

FIG. 2b is a graph illustrating magnetic flux induced in the section of the object by the inspection device of FIG. 2a.

FIG. 3b is a graph illustrating magnetic flux induced in the section of the object by the inspection device of FIG. 3a.

FIG. 4b is a graph illustrating magnetic flux induced in the section of the object by the inspection device of FIG. 4a.

DESCRIPTION OF THE PREFERRED EMBODIMENTS

The present invention is directed to magnetic inspection devices which use a simple DC magnetic saturation method for a reliable through-wall detection of structural faults such as axial slits in a magnetically permeable elongated object to be tested. As will be explained below more fully with respect to the preferred embodiments, two necessary conditions for reliable detection are achieved by the present invention. First, the inspection device of the present invention magnetically saturates or nearly-saturates a magnetically permeable elongated object to be tested. Second, the inspection device of the present invention induces substantial eddy currents so that eddy current changes representative of structural faults can be readily detected. The previous two conditions will hereinafter be referred to as the "necessary conditions".

Figure 1A:
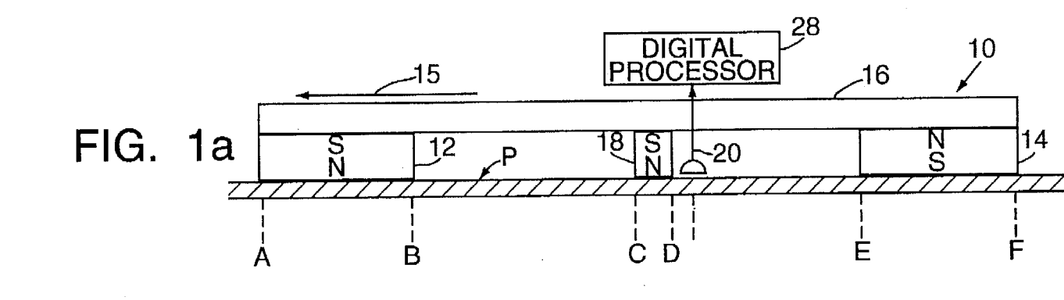
FIG. 1a schematically illustrates an embodiment of the magnetic inspection device along a longitudinal section of a magnetically permeable elongated object.

FIG. 1a illustrates schematically the operation of one preferred embodiment of a magnetic inspection device 10 for nondestructively inspecting a magnetically permeable elongated object such as a pipe P for structural faults. For clarity, only the top portion of the device 10 is shown and only the top longitudinal section of the pipe wall W is illustrated as being inspected by the device. Preferably, the inspection device extends substantially circumaxially about the object and may be located either externally of the object (as shown) or internally of the object. For example, an internal magnetic inspection device is illustrated in my U.S. Pat. No. 5,414,353.

The inspection device 10 includes a permanent magnet having first and second primary poles 12 and 14 for inducing a primary magnetic flux in the pipe wall. Each of the primary poles 12 and 14 is oppositely poled relative to one another and is radially polarized relative to the pipe P. The inspection device as shown in FIG. 1a moves leftwardly relative to the pipe P as indicated by the arrow 15 whereby the first primary pole 12 is upstream of the second primary pole 14 relative to inspection device movement. The primary poles 12 and 14 are magnetically coupled by a primary ferromagnetic member such as a ferromagnetic bar 16 which completes a magnetic flux circuit having a forward portion through a longitudinal section of the pipe P extending between the primary poles 12 and 14, and a return portion through the bar 16.

The inspection device shown in FIG. 1a further includes a flux-changing means embodied as an auxiliary magnetic pole 18 for inducing substantial eddy currents, whereby eddy current changes representative of structural faults can be readily detected. The auxiliary magnetic pole 18 has the same magnetic poling as the first primary pole 12 and is positioned on the inspection device between the primary poles 12 and 14. An eddy current change detecting means such as a sensor 20 is positioned on the inspection device downstream from the auxiliary pole 18 for detecting changes in eddy currents generated by the inspection device. The sensor can be a passive magnetic flux sensing coil but may also take other suitable forms such as Hall effect sensors or coils combined with integrators.

Figure 1B:
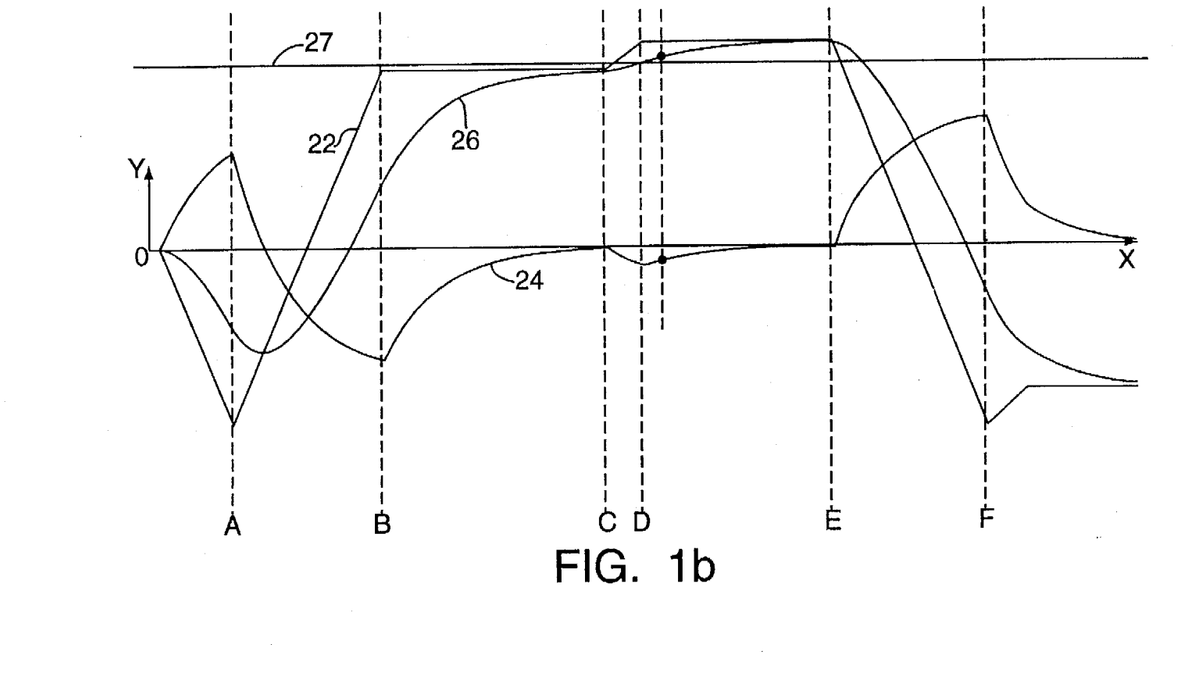

The operation of the magnetic inspection device 10 of FIG. 1a will now be explained with respect to the corresponding graph of FIG. 1b. FIG. 1b is a "freeze frame" illustrating the longitudinal magnetic flux and components thereof experienced in a corresponding longitudinal section of the pipe P of FIG. 1a as the inspection device moves leftwardly relative to the pipe P. A first flux component 22 shown in FIG. 1a is a static magnetic flux which is shown in straight-line approximation for clarity of explanation. The static magnetic flux is defined as the total longitudinal magnetic flux induced by the inspection device 10 under static or quasi-static operating conditions (i.e., at very slow speeds of relative movement of the inspection device and object) when eddy currents and their associated opposing magnetic flux are negligible. A second flux component 24 is due to SEEC (SEEC or opposing magnetic flux) which is defined as a magnetic flux generated by eddy currents opposing the static magnetic flux during relative movement of the inspection device and object to be tested. A dynamic magnetic flux 26 is the total magnetic flux experienced in the pipe wall P and is defined as the sum of the static magnetic flux and the SEEC or opposing magnetic flux components.

Referring to FIGS. 1a and 1b, as the inspection device moves leftwardly relative to the pipe P, the static magnetic flux 22 induced in the portion of the pipe wall adjacent the upstream edge of the first primary pole 12 (at position A) levels off in magnitude. The pipe wall is then magnetized in the portion of the adjacent pipe wall extending over the width of the first primary pole 12 (position A to position B) such that the portion of the pipe wall adjacent to the downstream edge of the first primary pole 12 (position B) is magnetized in the opposite direction relative to the portion of the pipe wall adjacent to position A. The static magnetic flux 22 moves leftwardly with the inspection device 10 relative to the pipe P, whereby the pipe experiences a changing magnetic flux. This changing magnetic flux induces SEECs (and their associated SEEC or opposing magnetic flux 24) along the portion of the pipe wall extending from the width of the first primary pole 12 (from position A to position B). The opposing magnetic flux 24 is fully developed within the pipe wall adjacent to the downstream edge of the first primary pole 12 (position B).

These eddy currents and associated opposing magnetic flux 24 retard the diffusion of the magnetic flux through the adjacent pipe wall and oppose magnetic saturation because the fully developed opposing magnetic flux 24 has a subtractive effect on the total or dynamic magnetic flux 26 (i.e., dynamic magnetic flux equals the static magnetic flux minus the opposing magnetic flux). This subtractive effect of the opposing magnetic flux 24 on the dynamic magnetic flux 26 is experienced within the adjacent portion of the pipe wall extending from the upstream edge of the first primary pole 12 to the upstream edge of the auxiliary pole 18 (from position A to position C), whereby the dynamic magnetic flux 26 in such portion of the pipe wall is not sufficient to drive the pipe into saturation.

The eddy currents decay over the portion of the pipe wall extending from the downstream edge of the first primary pole 12 to the upstream edge of the auxiliary pole 18 (from position B to position C), whereby the SEEC or opposing magnetic flux 24 is decreased in magnitude and consequently the dynamic magnetic flux 26 is increased in magnitude so that at the upstream edge of the auxiliary pole 18 (position C) the adjacent portion of the pipe wall is in near-saturation.

Over the portion of the pipe wall extending over the width of the auxiliary pole 18 (from position C to position D), the auxiliary pole 18 changes or increases the magnitude of the static magnetic flux 22 to thereby induce additional eddy currents, and to place the tested object into magnetic saturation (above magnetic saturation line 27). These additional eddy currents are fully developed in the portion of the pipe wall adjacent to the downstream edge of the auxiliary pole 18 (position D). The additional eddy currents tend to generate an SEEC or opposing magnetic flux 24 to impede saturation of the pipe wall by subtracting from the static magnetic flux and thereby reducing the dynamic magnetic flux below a saturation level. However, the additional eddy currents are insufficient to overcome the direct effect of the auxiliary pole 18 and decay over a portion of the pipe wall extending from the downstream edge of the auxiliary pole 18 to the upstream edge of the second primary pole 14 (position D to position E) such that the SEEC or opposing magnetic flux 24 is decreased. Consequently the dynamic magnetic flux 26 is increased above the saturation level at position D. The sensor 20 is positioned downstream from the auxiliary pole 18 and position D adjacent to a portion of the pipe wall where the dynamic magnetic flux 26 is in magnetic saturation and where the eddy currents have not decayed for eddy current change detection, thus satisfying the necessary conditions for structural fault detection. A digital processor 28, such as a computer, communicates with the sensor 20 for determining the location and magnitude of structural faults along the object to be tested in response to signals generated by the sensor 20 when detecting changes in eddy currents.

The additional eddy currents excited by the auxiliary pole 18 decay toward zero over the portion of the pipe wall extending from the sensor 20 to the upstream edge of the second primary pole 14 (position D to position E) such that at the upstream edge of the second primary pole 14 (position E), the adjacent portion of the pipe wall is magnetically saturated with no eddy currents flowing. Finally, over the portion of the pipe wall extending over the width of the second primary pole 14 (position E to position F), the pipe wall is magnetized in the opposite direction and eventually the flux returns to a residual value.

Figure 2A:
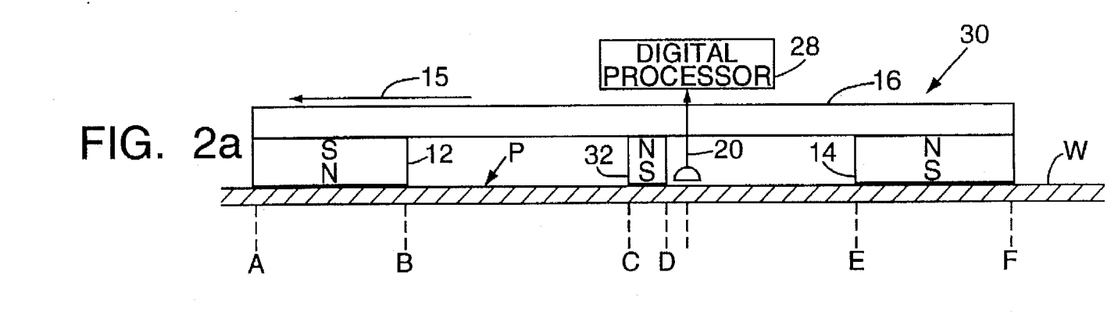
FIG. 2a schematically illustrates a second embodiment of the magnetic inspection device along a longitudinal section of a magnetically permeable elongated object.

FIG. 2a illustrates schematically the operation of another preferred embodiment of a magnetic inspection device 30 for nondestructively inspecting a magnetically permeable elongated object such as a pipe P for structural faults. Like elements with the previous embodiment will be labeled with like reference numerals. The inspection device 30 includes a permanent magnet having first and second primary poles 12 and 14, respectively. Each of the primary poles 12 and 14 is oppositely poled relative to one another and is radially polarized relative to the pipe P. The inspection device as shown in FIG. 2a moves leftwardly relative to the pipe P, whereby the first primary pole 12 is upstream of the second primary pole 14. The primary poles 12 and 14 are magnetically coupled by a ferromagnetic bar 16 which completes a magnetic flux circuit having a forward portion through a longitudinal section of the pipe P extending between the primary poles 12 and 14, and a return portion through the bar 16.

The inspection device shown in FIG. 2a further includes an auxiliary magnetic pole 32 having the opposite poling as the first primary pole 12 and positioned on the inspection device between the primary poles 12 and 14. (Note that the auxiliary pole 32 is oppositely poled relative to the auxiliary pole 18 illustrated in FIG. 1A.) A sensor 20 is positioned on the inspection device downstream from the auxiliary pole 32 for detecting changes in eddy currents generated by the inspection device.

Figure 2B:
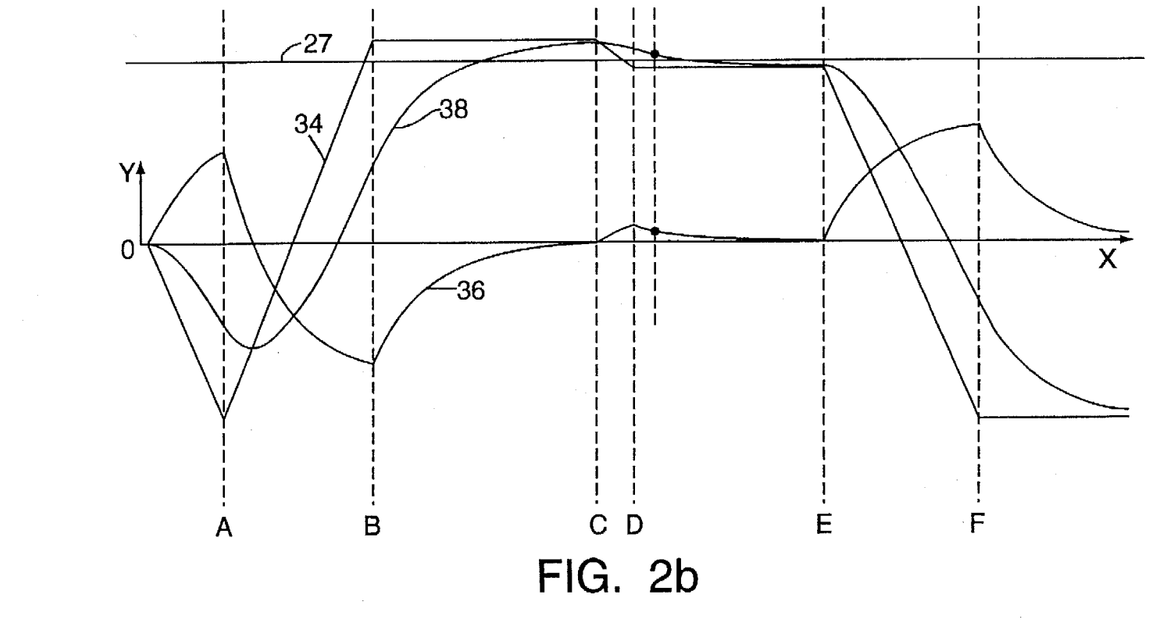

The operation of the magnetic inspection device 30 of FIG. 2a will now be explained with respect to the corresponding graph of FIG. 2b. As the inspection device moves leftwardly relative to the pipe P, a static magnetic flux 34 induced in the pipe wall adjacent the first primary pole 12 (at position A) levels off in magnitude. The pipe wall is then magnetized in the portion of the adjacent pipe wall extending over the width of the first primary pole 12 (position A to position B) such that the portion of the pipe wall adjacent to the downstream edge of the first primary pole 12 (position B) is magnetized in the opposite direction relative to the portion of the pipe wall adjacent to position A. The static magnetic flux moves leftwardly with the inspection device 30 relative to the pipe P, whereby the pipe experiences a changing magnetic flux. This changing magnetic flux induces SEECs (and their associated SEEC or opposing magnetic flux 36) along the portion of the pipe wall extending over the width of the first primary pole 12 (from position A to position B). The opposing magnetic flux is fully developed within the pipe wall adjacent position B. These eddy currents and associated opposing magnetic flux 36 retard the diffusion of the magnetic flux through the adjacent pipe wall and oppose magnetic saturation. The subtractive effect of the opposing magnetic flux 36 on a dynamic magnetic flux 38 is experienced within the adjacent portion of the pipe wall extending from the upstream edge of the first primary pole 12 to the upstream edge of the auxiliary pole 32 (from position A to position C).

However, the eddy currents decay over the portion of the pipe wall extending from the downstream edge of the first primary pole 12 to the upstream edge of the auxiliary pole 32 (from position B to position C), whereby the SEEC or opposing magnetic flux 36 is decreased in magnitude and consequently the dynamic magnetic flux 38 is increased in magnitude so that from a position midway between the downstream edge of the pole 12 (position B) and the upstream edge of the auxiliary pole 32 (position C) the adjacent portion of the pipe wall is magnetically saturated (i.e., the dynamic magnetic flux 38 is above the magnetic saturation line 27).

Over the portion of the pipe wall extending over the width of the auxiliary pole 32 (from position C to position D), the auxiliary pole 32 changes or decreases the static magnetic flux 34 tending to drive the pipe wall out of saturation toward near-saturation, whereby the changing static magnetic flux 34 induces additional eddy currents. These additional eddy currents are fully developed in the portion of the pipe wall adjacent to the downstream edge of the auxiliary pole 32 (position D). The additional eddy currents generate an SEEC or opposing magnetic flux 36 which opposes the slight reduction in magnetic flux, and therefore actually tends to hold the pipe wall in magnetic saturation. The additional eddy currents decay over a portion of the pipe wall extending from the downstream edge of the auxiliary pole 32 to the upstream edge of the second primary pole 14 (position D to position E) such that the SEEC or opposing magnetic flux 36 is decreased and consequently the dynamic magnetic flux 38 is decreased below the saturation level (i.e. below the saturation line 27). However, the sensor 20 is positioned adjacent to a portion of the pipe wall downstream from the auxiliary pole 32 where the dynamic magnetic flux 38 is still in magnetic saturation and where the eddy currents have not decayed for eddy current change detection, thus satisfying the necessary conditions for structural fault detection. The digital processor 28 communicates with the sensor 20 for determining the location and magnitude of structural faults along the object to be tested in response to signals generated by the sensor 20.

The additional eddy currents excited by the auxiliary pole 32 decay toward zero over the portion of the pipe wall extending from the sensor 20 to the upstream edge of the second primary pole 14 (position D to position E) such that at the upstream edge of the second primary pole 14 (position E), the adjacent portion of the pipe wall is near magnetic saturation with no eddy currents flowing. Finally, over the portion of the pipe wall extending over the width of the second primary pole 14 (position E to position F), the pipe wall is magnetized in the opposite direction and eventually the flux returns to a residual value.

Figure 3A:
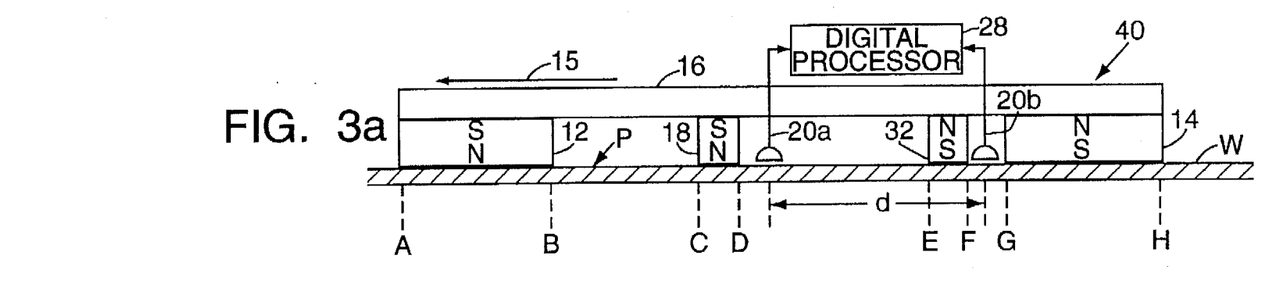
FIG. 3a schematically illustrates a third embodiment of the magnetic inspection device along a longitudinal section of a magnetically permeable elongated object.

FIG. 3a illustrates schematically the operation of A further preferred embodiment of a magnetic inspection device 40 which combines both of the auxiliary poles 18, 32 of the previous two embodiments. The inspection device 40 includes a permanent magnet having first and second primary poles 12 and 14, respectively. Each of the primary poles 12 and 14 is oppositely poled relative to one another and is radially polarized relative to the pipe P. The inspection device as shown in FIG. 3a moves leftwardly relative to the pipe P, whereby the first primary pole 12 is upstream of the second primary pole 14. The primary poles 12 and 14 are magnetically coupled by a ferromagnetic bar 16 which completes a magnetic flux circuit having a forward portion through a longitudinal section of the pipe P extending between the primary poles 12 and 14, and a return portion through the bar 16.

The inspection device shown in FIG. 3a further includes a first auxiliary magnetic pole 18 having the same poling as the first primary pole 12 and positioned on the inspection device between the primary poles 12 and 14. A second auxiliary magnetic pole 32 has the opposite poling as the first primary pole and is positioned both downstream of the first auxiliary magnetic pole 18 and between the primary poles 12 and 14. First sensor 20a and second sensor 20b are positioned on the inspection device downstream from the first auxiliary pole 18 and the second auxiliary pole 32, respectively, for detecting changes in eddy currents generated by the inspection device.

The operation of the magnetic inspection device 40 of FIG. 3a will now be explained with respect to the corresponding graph of FIG. 3b. As the inspection device moves leftwardly relative to the pipe P, a static magnetic flux 42 induced in the pipe wall adjacent the first primary pole 12 (at position A) levels off in magnitude. The pipe wall is then magnetized in the portion of the adjacent pipe wall extending over the width of the first primary pole 12 (position A to position B) such that the portion of the pipe wall adjacent to the downstream edge of the first primary pole 12 (position B) is magnetized in the opposite direction relative to the portion of the pipe wall adjacent to position A. The static magnetic flux 42 moves leftwardly with the inspection device 40 relative to the pipe P, whereby the pipe experiences a changing magnetic flux. This changing magnetic flux induces SEECs (and their associated SEEC or opposing magnetic flux 44) along the portion of the pipe wall extending over the width of the first primary pole 12 (from position A to position B). The opposing magnetic flux 44 is fully developed within the pipe wall adjacent position B. These eddy currents and associated opposing magnetic flux 44 retard the diffusion of the magnetic flux through the adjacent pipe wall and oppose magnetic saturation. The subtractive effect of the opposing magnetic flux on the dynamic magnetic flux is experienced within the adjacent portion of the pipe wall extending from the upstream edge of the first primary pole 12 to the upstream edge of the first auxiliary pole 18 (from position A to position C), whereby a dynamic magnetic flux 46 in such portion of the pipe wall is not sufficient to drive the pipe into saturation.

The eddy currents decay over the portion of the pipe wall extending from the downstream edge of the first primary pole 12 to the upstream edge of the first auxiliary pole 18 (from position B to position C), whereby the SEEC or opposing magnetic flux 44 is decreased in magnitude and consequently the dynamic magnetic flux 46 is increased in magnitude so that at the upstream edge of the first auxiliary pole 18 (position C) the adjacent portion of the pipe wall is in near-saturation (i.e., the dynamic magnetic flux 46 is immediately below the magnetic saturation line 27).

Over the portion of the pipe wall extending over the width of the first auxiliary pole 18 (from position C to position D), the first auxiliary pole 18 changes or increases the static magnetic flux into saturation thereby inducing additional eddy currents. These additional eddy currents are fully developed in the portion of the pipe wall adjacent to the downstream edge of the first auxiliary pole 18 (position D). The additional eddy currents generate an SEEC or opposing magnetic flux 44 to impede saturation of the pipe wall by subtracting from the static magnetic flux 42 and thereby reducing the dynamic magnetic flux 46 below a saturation level. However, the additional eddy currents decay over a portion of the pipe wall extending from the downstream edge of the first auxiliary pole 18 to the upstream edge of the second auxiliary pole 32 (position D to position E) such that the SEEC or opposing magnetic flux 44 is decreased and consequently the dynamic magnetic flux 46 is increased above the saturation level. The first sensor 20a is positioned downstream from the first auxiliary pole 18 adjacent to a portion of the pipe wall where the dynamic magnetic flux 46 is in magnetic saturation and where the eddy currents have not decayed for eddy current change detection, thus satisfying the necessary conditions for structural fault detection.

The additional eddy currents excited by the first auxiliary pole 18 decay toward zero over the portion of the pipe wall extending from the first sensor 20a to the upstream edge of the second auxiliary pole 32 (position D to position E) such that at the upstream edge of the second auxiliary pole 32 (position E), the adjacent portion of the pipe wall is magnetically saturated with no eddy currents flowing.

Over the portion of the pipe wall extending over the width of the second auxiliary pole 32 (from position E to position F), the auxiliary pole 32 changes or decreases the previously increased static magnetic flux 42 to drive the pipe wall out of saturation into near-saturation, whereby the changing static magnetic flux 42 induces additional eddy currents. These additional eddy currents are fully developed in the portion of the pipe wall adjacent to the downstream edge of the second auxiliary pole 32 (position F). The additional eddy currents generate an SEEC or opposing magnetic flux 44 which opposes the slight reduction in magnetic flux, and therefore actually tends to drive the pipe wall back into magnetic saturation. The additional eddy currents decay over a portion of the pipe wall extending from the downstream edge of the second auxiliary pole 32 to the upstream edge of the second primary pole 14 (position F to position G) such that the SEEC or opposing magnetic flux 44 is decreased and consequently the dynamic magnetic flux 46 is decreased toward the saturation level. However, the second sensor 20b is positioned adjacent to a portion of the pipe wall downstream from the second auxiliary pole 32 where the dynamic magnetic flux 46 is still in magnetic saturation and where the eddy currents have not decayed for eddy current change detection, thus satisfying the necessary conditions for structural fault detection.

The additional eddy currents excited by the second auxiliary pole 32 decay over the portion of the pipe wall extending from the second sensor 20b to the upstream edge of the second primary pole 14 (position F to position G) such that at the upstream edge of the second primary pole 14 (position G), the adjacent portion of the pipe wall is magnetically saturated with weak residual eddy currents flowing. Finally, over the portion of the pipe wall extending over the width of the second primary pole 14 (position G to position H), the pipe wall is magnetized in the opposite direction.

A drawback with employing an eddy current-magnetic saturation approach is that the first sensor 20a passively generates an induced signal $S_1$ comprising both an eddy current change signal component $s_{seec}$ and an unwanted magnetic flux leakage (MFL) signal component $s_{mfl}$ representative of other types of faults such as loss of metallic cross-sectional area (LMA) or localized faults (LFs). The problem of distinguishing the $s_{seec}$ component from the $s_{mfl}$ component is solved by employing the second sensor 20b which passively generates an induced signal $S_2$ comprising an eddy current change signal component $s_{seec}$ as well as a magnetic flux leakage signal component $s_{mfl}$.

The two signals $S_1$ and $S_2$ can then be used to implement a combined SEEC/MFL inspection method. In this case, the signal $S_1$ measured by the first sensor 20a, and the signal $S_2$ measured by the second sensor 20b, are used to determine the signal components $s_{mfl}$ and $s_{seec}$ that are indicative of flaws of the MFL and SEEC type. As a first approximation, a linear relationship between these signal components can be established by the following equations.

$$S_1(x) = A s_{mfl}(x) + B s_{seec}(x+d) \quad (1)$$
$$S_2(x+d) = C s_{mfl}(x+d) + D s_{seec}(x+d) \quad (2)$$

Here, A, B, C and D are constants that depend on the geometry of the sensor head and the pipe as well as the inspection velocity, x is the longitudinal coordinate along the length of the pipe, and d is the distance between the sensors 20a and 20b. The coordinates of the signal of the second sensor 20b can then be shifted by the distance d to obtain the signal detected by the second sensor 20b at coordinate x, i.e., $S_2(x)$. After this shifting operation, $s_{mfl}(x)$ (i.e., the true MFL) signal) and $s_{seec}(x)$ (the true SEEC signal) can be determined from the signals $S_1(x)$ and $S_2(x)$, the signals sensed by the sensors 20a and 20b, respectively. If linear superposition is assumed, this can be done by solving equations (1) and (2) as simultaneous equations. The digital processor 28 communicates with the sensors 20a and 20b and is used either on-line or off-line for solving these computations and thus determining the location and magnitude of a structural fault.

Figure 4A:
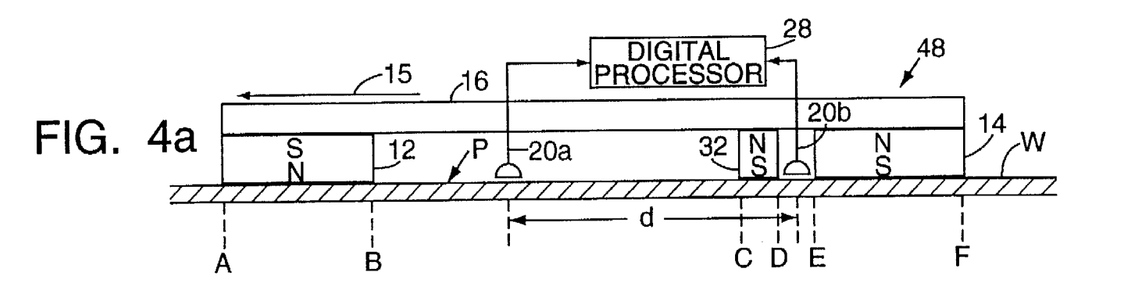
FIG. 4a schematically illustrates a fourth embodiment of the magnetic inspection device along a longitudinal section of a magnetically permeable elongated object.

FIG. 4a illustrates schematically the operation of a preferred embodiment of a magnetic inspection device 48 for nondestructively inspecting a magnetically permeable elongated object such as a pipe P for structural faults. In this embodiment, only one auxiliary pole is employed with two sensors. Like elements with the previous embodiments will be labelled with like reference numerals. The inspection device 48 includes a permanent magnet having first and second primary poles 12 and 14, respectively. Each of the primary poles 12 and 14 is oppositely poled relative to one another and is radially polarized relative to the pipe P. The inspection device as shown in FIG. 4a moves leftwardly relative to the pipe P, whereby the first primary pole 12 is upstream of the second primary pole 14. The primary poles 12 and 14 are magnetically coupled by a ferromagnetic bar 16 which completes a magnetic flux circuit having a forward portion through a longitudinal section of the pipe P extending between the primary poles 12 and 14, and a return portion through the bar 16.

The inspection device shown in FIG. 4a further includes a first sensor 20a positioned on the inspection device downstream from the first primary pole 12 for detecting changes in eddy currents generated by the inspection device. An auxiliary magnetic pole 32 has the opposite poling as the first primary pole 12 and is positioned downstream from the first sensor 20a and between the primary poles 12 and 14. A second sensor 20b for detecting eddy current changes is positioned on the inspection device downstream from the auxiliary pole 32 and between the primary poles 12 and 14.

Figure 4B:
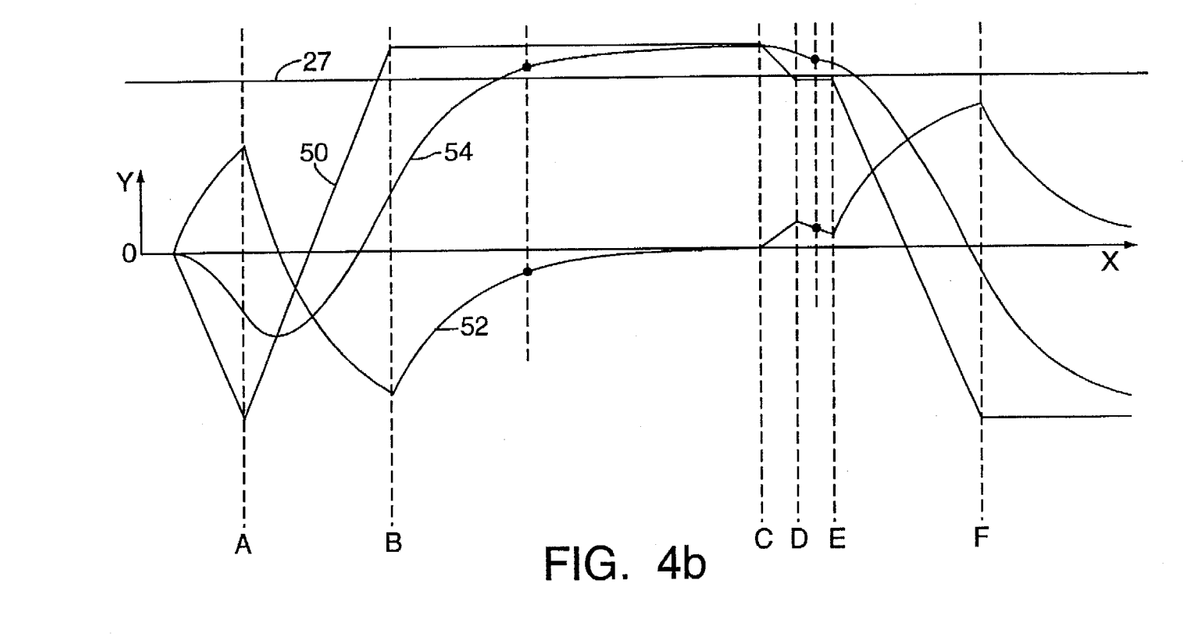

The operation of the magnetic inspection device 48 of FIG. 4a will now be explained with respect to the corresponding graph of FIG. 4b. As the inspection device 48 moves leftwardly relative to the pipe P, a static magnetic flux 50 induced in the pipe wall adjacent the first primary pole 12 (at position A) levels off in magnitude. The pipe wall is then magnetized in the portion of the adjacent pipe wall extending over the width of the first primary pole 12 (position A to position B) such that the portion of the pipe wall adjacent to the downstream edge of the first primary pole 12 (position B) is magnetized in the opposite direction relative to the portion of the pipe wall adjacent to position A. The static magnetic flux 50 moves leftwardly with the inspection device 48 relative to the pipe P, whereby the pipe experiences a changing magnetic flux. This changing magnetic flux induces SEECs (and their associated SEEC or opposing magnetic flux 52) along the portion of the pipe wall extending over the width of the first primary pole 12 (from position A to position B). The opposing magnetic flux 52 is fully developed within the pipe wall adjacent position B.

These eddy currents and associated opposing magnetic flux 52 retard the diffusion of the magnetic flux through the adjacent pipe wall and oppose magnetic saturation. This subtractive effect of the opposing magnetic flux on the dynamic magnetic flux is experienced within the adjacent portion of the pipe wall extending from the upstream edge of the first primary pole 12 to the upstream edge of the auxiliary pole 32 (from position A to position C).

The eddy currents decay to zero over the portion of the pipe wall extending from the downstream edge of the first primary pole 12 to the upstream edge of the auxiliary pole 32 (from position B to position C), whereby the SEEC or opposing magnetic flux 52 is decreased in magnitude and consequently a dynamic magnetic flux 54 is increased in magnitude so that immediately upstream from the sensor 20a, an adjacent portion of the pipe wall is magnetically saturated. The first sensor 20a is positioned downstream from the first primary pole 12 adjacent to a portion of the pipe wall where the eddy currents have not decayed for eddy current change detection, thus satisfying the necessary conditions for structural fault detection. At a portion of the pipe wall adjacent the upstream edge of the auxiliary pole 32 (position C) the eddy currents have completely decayed so as to allow deep magnetic saturation of the object to be tested (i.e., the dynamic magnetic flux 54 is well-above the magnetic saturation line 27).

Over the portion of the pipe wall extending over the width of the auxiliary pole 32 (from position C to position D), the auxiliary pole 32 changes or decreases toward the saturation level the static magnetic flux 50 in the adjacent pipe wall, whereby the changing static magnetic flux 50 induces additional eddy currents. These additional eddy currents are fully developed in the portion of the pipe wall adjacent to the downstream edge of the auxiliary pole 32 (position D). The additional eddy currents generate an SEEC or opposing magnetic flux 52 which opposes the reduction in magnetic flux, and therefore actually tends to keep the pipe in magnetic saturation. The additional eddy currents decay over a portion of the pipe wall extending from the downstream edge of the auxiliary pole 32 to the upstream edge of the second primary pole 14 (position D to position E) such that the SEEC or opposing magnetic flux 52 is decreased and consequently the dynamic magnetic flux 54 is decreased toward the saturation level. However, the second sensor 20b is positioned adjacent to a portion of the pipe wall downstream from the auxiliary pole 32 where the dynamic magnetic flux 54 is still in magnetic saturation and where the decaying eddy currents have not decayed for eddy current change detection, thus satisfying the necessary conditions for structural fault detection.

The additional eddy currents excited by the auxiliary pole 32 decay toward zero over the portion of the pipe wall extending from the downstream edge of the auxiliary pole 32 to the upstream edge of the second primary pole 14 (position D to position E) such that at the upstream edge of the second primary pole 14 (position E), the adjacent portion of the pipe wall is magnetically saturated with weak residual eddy currents flowing. Finally, over the portion of the pipe wall extending over the width of the second primary pole 14 (position E to position F), the pipe wall is magnetized in the opposite direction.

The signals generated by the sensors 20a and 20b may be simultaneously solved by the digital processor 28, as explained more fully in the previous embodiment, to accurately discriminate structural faults from magnetic leakage faults.

A difficulty with the previously described auxiliary pole approach is that the sensors are typically mounted on the inspection device in a spring-loaded assembly which does not include the auxiliary poles. This assembly requires a considerable amount of mounting space because the assembly must provide ample space for positional adjustment of the sensors in both the radial and longitudinal directions. As such, the size of the spring-loaded assembly makes it difficult to mount the sensors supported therein at their optimum positions close to the downstream edge of the auxiliary poles. This difficulty can be solved by mounting the auxiliary poles and the sensors close to and in fixed position relative to each other within a combined assembly or module. The entire auxiliary pole/sensor module can then be spring mounted within the inspection device between the primary poles.

Figure 5:
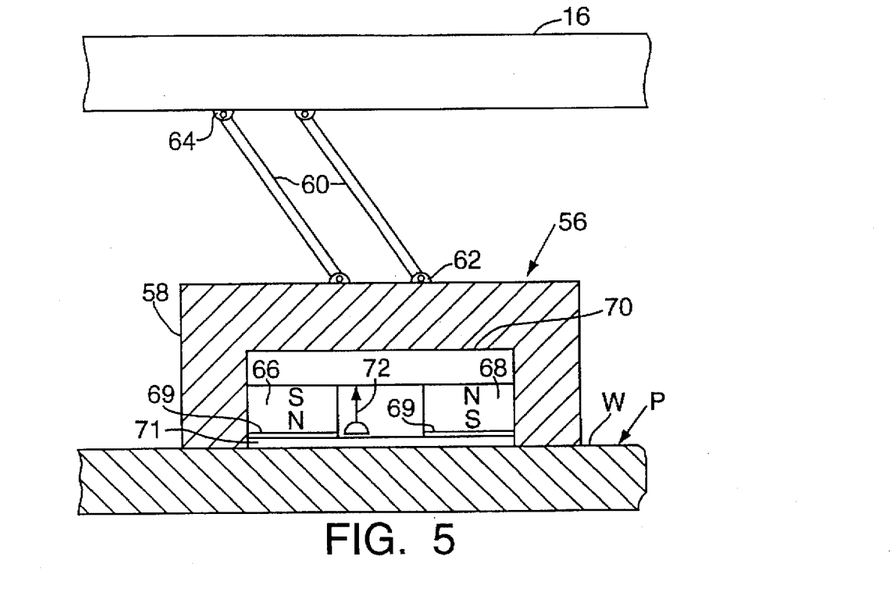
FIG. 5 schematically illustrates an embodiment of an auxiliary pole/sensor module.

FIG. 5 schematically illustrates such an auxiliary pole/sensor module indicated generally at 56 which serves as a substitution for the auxiliary pole 18 and the sensor 20 shown in FIG. 1a. The module 56 is mounted on the inspection device 10 longitudinally between the primary poles 12, 14 at a location on the inspection device otherwise occupied by the auxiliary pole 18 and the sensor 20. The module 56 includes a housing 58 which is sectioned to reveal an auxiliary pole/sensor assembly therein. The housing is radially adjustably coupled to the ferromagnetic bar 16 of the inspection device 10 (FIG. 1a) for positioning adjacent an elongated object to be tested such as the pipe P. More specifically, the housing 58 is adjustably coupled to the ferromagnetic bar 16 by means of parallel link members 60, 60 each having first and second longitudinal ends which are respectively pivotally coupled to the housing 58 and the ferromagnetic bar 16 by means of hinge members 62, 62.

The auxiliary pole/sensor assembly within the housing 58 includes a flux-changing means embodied as an auxiliary permanent magnet having first and second auxiliary poles 66, 68 for inducing an auxiliary magnetic flux in the pipe wall between the auxiliary poles which changes or increases the static magnetic flux induced by the primary poles. Each of the auxiliary poles 66, 68 is oppositely poled relative to one another and is radially polarized relative to the pipe P. The auxiliary poles 66, 68 each preferably supports a pole piece 69 made from a hard metal such as steel to prevent abrasive wear of the auxiliary poles. A bushing 71 made from an abrasive-resistant non-magnetic material such as ultra high molecular weight polyethylene (UHM) may be interposed between the pole pieces 69, 69 and the object to be tested to further prevent wear. The auxiliary poles 66, 68 are magnetically coupled by an auxiliary ferromagnetic member or bar 70 which completes an auxiliary magnetic flux circuit having a forward portion through a longitudinal section of the pipe P extending between the auxiliary poles 66, 68, and a return portion through the auxiliary bar 70. The auxiliary pole/sensor assembly further includes a sensor 72 positioned on the inspection device downstream from the auxiliary pole 66 for detecting changes in eddy currents generated by the inspection device. The sensor 72 communicates with a digital processor, such as the processor 28 shown in FIG. 1a, for determining the location and magnitude of structural faults along the object to be tested in response to signals generated by the sensor 72 when detecting changes in eddy currents within the object such as the wall of the pipe P.

The housing 58 permits the auxiliary poles 66, 68 and the sensor 72 to be fixedly positioned relative to each other as a unit therein. Accordingly, the sensor 72 may be positioned closely downstream of the first auxiliary pole 66 for optimum detection of eddy current changes.

As was stated above, the separately positioned auxiliary pole 18 and sensor 20 shown in FIG. 1a are replaced with the housing 58 of FIG. 5. Accordingly, the portion of the pipe wall extending between the auxiliary poles is located approximately midway between the primary poles 12, 14 (shown in FIG. 1 near position C) where such portion is in near magnetic saturation due to the influence of the static magnetic flux induced by the primary poles 12, 14 and has substantially no eddy currents induced by the primary poles because such eddy currents have decayed.

The auxiliary pole/sensor assembly of FIG. 5 is distinguishable from the single auxiliary pole 18 employed in FIG. 1a in that the assembly has two oppositely poled auxiliary poles 66, 68 which cooperate with the auxiliary bar 70 to provide an auxiliary magnetic circuit which is independent of the primary magnetic circuit comprising the primary magnetic poles 12, 14 and ferromagnetic bar 16 shown in FIG. 1a. The independent auxiliary circuit permits the auxiliary/sensor assembly to change or increase the static magnetic flux in a localized longitudinal portion of the pipe wall extending between the auxiliary poles, as opposed to the more extended longitudinal portion between the auxiliary pole 18 and the second primary pole 14 shown in FIGS. 1a and 1b.

As the inspection device 10 of FIG. 1a substituted with the module 56 of FIG. 5 moves leftwardly relative to the pipe P to be tested, the sensor 72 is located downstream of the first auxiliary pole 66. The auxiliary magnetic flux induced in the portion of the pipe wall extending between the first and second auxiliary poles 66 and 68 changes or increases in magnitude the static magnetic flux induced by the primary poles 12, 14 to thereby induce additional eddy currents which are fully developed in the portion of the pipe wall adjacent to the downstream edge of the first auxiliary pole 66. The additional eddy currents tend to generate an SEEC or opposing magnetic flux to impede saturation of the pipe wall by subtracting from the static magnetic flux and thereby reducing the dynamic magnetic flux below a saturation level. However, the additional eddy currents are insufficient to overcome the direct effect of the auxiliary pole/sensor assembly and decay over a portion of the pipe wall extending from the downstream edge of the first auxiliary pole 66 to the upstream edge of the second auxiliary pole 68 such that the SEEC or opposing magnetic flux is decreased. Consequently the dynamic magnetic flux is increased above the saturation level in the portion of the pipe wall adjacent to the sensor 72. The sensor 72) is positioned adjacent to a portion of the pipe wall where the dynamic magnetic flux is in magnetic saturation and where the eddy currents have not decayed for eddy current change detection so as to satisfy the necessary conditions for structural fault detection.

The auxiliary pole/sensor assembly shown in FIG. 5 may be modified in various ways such as by removing the second auxiliary pole 68 so as provide a single auxiliary pole assembly closely resembling the embodiment and operation of the present invention shown in FIGS. 1a and 1b except that the flux return path for such a single auxiliary pole assembly would be generally through the air since the housing 58 is not sufficiently magnetically coupled to the ferromagnetic bar 16 for a substantial ferromagnetic flux return path. Alternatively, the single auxiliary pole could be reversed in polarity so as resemble the embodiment and operation of the present invention shown in FIGS. 2a and 2b. Furthermore, each of the auxiliary poles 66, 68 may be changed in polarity so as to resemble the embodiment and operation of the present invention shown in FIGS. 2a and 2b.

Figure 6:
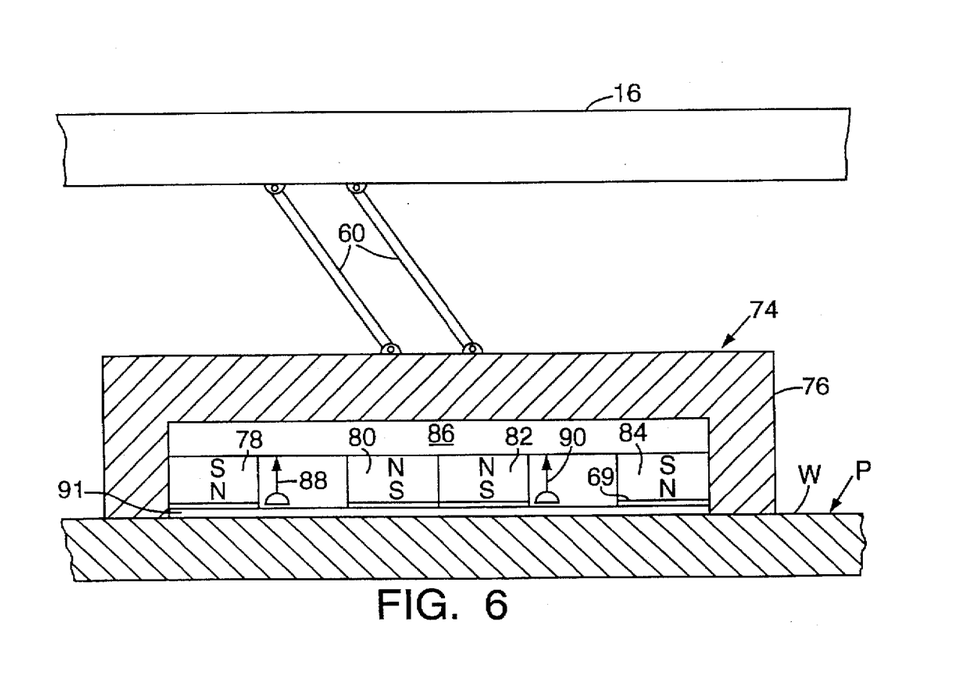
FIG. 6 schematically illustrates another embodiment of an auxiliary pole/sensor module.

FIG. 6 schematically illustrates another embodiment of an auxiliary pole/sensor module generally indicated at 74 which serves as a substitution for the auxiliary poles 18, 32 and the sensors 20a, 20b shown in FIG. 3a. The module 74 is mounted on the inspection device 40 longitudinally between the primary poles 12, 14 at a location on the inspection device otherwise occupied by the auxiliary poles 18, 32 and the sensors 20a, 20b. The module 74 includes a housing 76 which is sectioned to reveal an auxiliary pole/ sensor assembly therein. The housing is radially adjustably coupled to the ferromagnetic bar 16 by means of the parallel link members 60, 60 as was fully in the embodiment of FIG. 5.

The auxiliary pole/sensor assembly within the housing 74 includes a flux-changing means embodied as two discrete auxiliary permanent magnets. A first auxiliary magnet has first and second auxiliary poles 78, 80 constituting a first set of auxiliary poles for inducing a first auxiliary magnetic flux in the pipe wall between the auxiliary poles 78, 80 which changes or increases the static magnetic flux induced by the primary poles. Each of the auxiliary poles 78, 80 is oppositely poled relative to one another and is radially polarized relative to the pipe P. The auxiliary poles 78, 80 are magnetically coupled by an auxiliary ferromagnetic member or bar 86 which completes an auxiliary magnetic flux circuit having a forward portion through a longitudinal section of the pipe P extending between the auxiliary poles 78, 80, and a return portion through the auxiliary bar 86. The auxiliary pole/sensor assembly further includes a first sensor 88 positioned on the inspection device downstream from the auxiliary pole 78 for detecting changes in eddy currents generated by the inspection device. The first sensor 88 communicates with a digital processor, such as the processor 28 shown in FIG. 3a, for determining the location and magnitude of structural faults along the object to be tested in response to signals generated by the sensor 88 when detecting changes in eddy currents within the object such as the wall of the pipe P.

The second permanent magnet of the flux-changing means has third and fourth auxiliary poles 82, 84 constituting a second set of auxiliary poles for inducing a second auxiliary magnetic flux in the pipe wall between the auxiliary poles 82, 84 in a longitudinal direction opposite to that of the first auxiliary magnetic flux which changes or decreases the static magnetic flux induced by the primary poles. Each of the auxiliary poles 82, 84 is oppositely poled relative to one another and is radially polarized relative to the pipe P. The auxiliary poles 82, 84 are magnetically coupled by the auxiliary ferromagnetic bar 86 which completes a second auxiliary magnetic flux circuit having a forward portion through a longitudinal section of the pipe P extending between the auxiliary poles 82, 84, and a return portion through the auxiliary bar 86. The auxiliary pole/sensor assembly further includes a second sensor 90 positioned on the inspection device downstream from the third auxiliary pole 82 for detecting changes in eddy currents generated by the inspection device. The second sensor 90 communicates with a digital processor, such as the processor 28 shown in FIG. 3a, for determining the location and magnitude of structural faults along the object to be tested in response to signals generated by the sensor 90 when detecting changes in eddy currents within the object such as the wall of the pipe P. Each of the auxiliary poles 78, 80, 82, 84 preferably supports a pole piece 69 made from a hard metal such as steel. A bushing 91 made from UHM may be interposed between the pole pieces 69, 69 and the object to be tested to prevent further wear. The digital processor 28 may be employed for determining a magnetic flux leakage component and an eddy current change component of the signals generated by the sensors 88 and 90 by means of solving simultaneous equations as was fully discussed in the embodiment shown in FIGS. 3a and 3b.

The housing 76 permits the auxiliary poles 78, 80, 82, 84 and the sensors 88, 90 to be fixedly positioned relative to each other as a unit therein. Accordingly, the sensors 88, 90 may respectively be positioned closely downstream of the auxiliary poles 78, 82 for optimum detection of eddy current changes.

As was stated above, the separately positioned auxiliary poles 18, 32 and the sensor 20a, 20b shown in FIG. 3a are replaced with the housing 76 of FIG. 6. Accordingly, the portion of the pipe wall extending between the auxiliary poles is located approximately midway between the primary poles 12, 14 (shown in FIG. 3a near position C) where such portion is at least near magnetic saturation due to the influence of the static magnetic flux induced by the primary poles 12, 14 and has substantially no eddy currents induced by the primary poles because such eddy currents have decayed.

The auxiliary pole/sensor assembly of FIG. 6 is distinguishable from the auxiliary pole 18 employed in FIG. 3a in that the assembly has two oppositely poled auxiliary poles 78, 80 which cooperate with the auxiliary bar 86 to provide a first auxiliary magnetic circuit which is independent of the primary magnetic circuit comprising the primary magnetic poles 12, 14 and ferromagnetic bar 16 shown in FIG. 1a. Similarly, the auxiliary pole/sensor assembly of FIG. 6 is distinguishable from the auxiliary pole 32 employed in FIG. 3a in that the assembly has two oppositely poled auxiliary poles 82, 84 which cooperate with the auxiliary bar 86 to provide a second auxiliary magnetic circuit which is independent of the primary magnetic circuit comprising the primary magnetic poles 12, 14 and ferromagnetic bar 16 shown in FIG. 1a. The first auxiliary circuit permits the auxiliary/sensor assembly to increase the static magnetic flux in a localized longitudinal portion of the pipe wall extending between the auxiliary poles 78, 80, and the second auxiliary circuit permits the auxiliary/sensor assembly to decrease the static magnetic flux in a localized longitudinal portion of the pipe wall extending between the auxiliary poles 82, 84, as opposed to the more extended longitudinal portions as discussed and shown with respect to the embodiment of FIGS. 3a and 3b.

As the inspection device with the housing 76 carrying the auxiliary pole/sensor assembly (shown in FIG. 6) moves leftwardly relative to the pipe P to be tested, the first sensor 88 is located downstream of the first auxiliary pole 78. The auxiliary magnetic flux induced in the portion of the pipe wall extending between the first and second auxiliary poles 78 and 80 changes or increases in magnitude the static magnetic flux induced by the primary poles to thereby induce additional eddy currents which are fully developed in the portion of the pipe wall adjacent to the downstream edge of the first auxiliary pole 78. The additional eddy currents tend to generate an SEEC or opposing magnetic flux to impede saturation of the pipe wall by subtracting from the static magnetic flux and thereby reducing the dynamic magnetic flux below a saturation level. However, the additional eddy currents are insufficient to overcome the direct effect of the auxiliary pole/sensor assembly and decay over a portion of the pipe wall extending from the downstream edge of the first auxiliary pole 78 to the upstream edge of the second auxiliary pole 80 such that the SEEC or opposing magnetic flux is decreased. Consequently the dynamic magnetic flux is increased above the saturation level in the portion of the pipe wall adjacent to the first sensor 88. The first sensor 88 is positioned adjacent to a portion of the pipe wall where the dynamic magnetic flux is in magnetic saturation and where the eddy currents have not decayed so as to satisfy the necessary conditions for structural fault detection.

Similarly, the second auxiliary magnetic flux induced in the portion of the pipe wall extending between the third and fourth auxiliary poles 82 and 84 changes or decreases in magnitude the static magnetic flux induced by the primary poles to thereby induce additional eddy currents which are fully developed in the portion of the pipe wall adjacent to the downstream edge of the third auxiliary pole 82. The additional eddy currents generate an SEEC or opposing magnetic flux to oppose the decrease in magnitude of the static magnetic flux, and therefore actually tend to drive the pipe wall back into magnetic saturation such that the dynamic magnetic flux is above saturation in a portion of the pipe wall adjacent to the second sensor 90. The second sensor 90 is positioned adjacent to a portion of the pipe wall where the dynamic magnetic flux is in magnetic saturation and where the eddy currents have not decayed so as to satisfy the necessary conditions for structural fault detection.

Figure 3B:
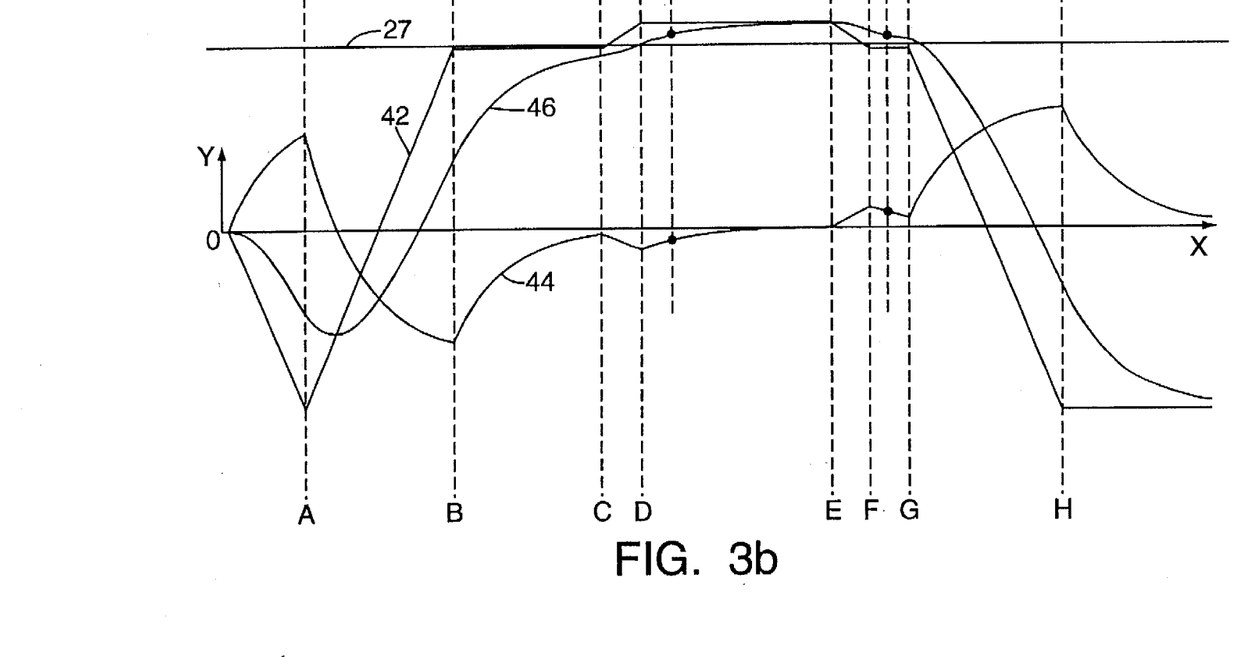

The auxiliary pole/sensor assembly shown in FIG. 6 may be modified in various ways such as by removing the fourth auxiliary pole 84 so as to provide an auxiliary pole assembly closely resembling the embodiment and operation of FIGS. 3a and 3b. Alternatively, the polarities in the above-modification may be reversed. Furthermore, each of the auxiliary poles 78, 80, 82, 84 may be changed in polarity.

While the present invention has been described in several embodiments, it will be understood that numerous modifications and substitutions can be made without departing from the spirit and scope of the invention. For example, the permanent magnets in the preferred embodiments can be replaced by other suitable devices such as electromagnets. Further, additional eddy current change detecting means can be positioned near each other in order to gather more precise data of the elongated object to be inspected. The eddy current change detecting means employed as SF sensors can also be used with a combination of LMA and LF sensors which are both normally located between longitudinally spaced opposite magnetic poles. In addition, the relative movement between the magnetic inspection device and object to be inspected can, of course, be produced by either moving the object relative to a stationary inspection device, by moving the device relative to a stationary object, or by moving both the device and the object at different speeds relative to each other. Accordingly, the present invention has been described in several preferred embodiments by way of illustration, rather than limitation.

What is claimed is:

1. A method for nondestructively inspecting an elongated magnetically permeable object for structural faults, comprising the steps of:

inducing a static magnetic flux by means of a magnet device through a longitudinal section of a magnetically permeable elongated object to at least a near-saturation level, the longitudinal section extending between first and second opposite primary poles of the magnet device;

changing the magnitude of the induced static magnetic flux at a portion of the object by means of at least one flux-changing means positioned on the magnet device between the first and second primary poles;

moving the magnet device and the induced static magnetic flux progressively and longitudinally relative to the object, whereby circumaxial eddy currents and associated opposing magnetic fluxes are induced in portions of the moving object adjacent to the first primary pole and the flux-changing means, the first primary pole being positioned upstream of the flux-changing means relative to magnet device movement such that at a portion of the object adjacent to the flux-changing means the eddy currents induced by the first primary pole have decayed and such portion of the object is generally at magnetic saturation;

generating at least one signal in a portion of the object downstream from the flux-changing means where combined static and opposing magnetic fluxes magnetically saturate such portion and where the eddy currents induced adjacent to the flux-changing means have not decayed so that eddy current changes representative of structural faults can be detected; and determining the location and magnitude of a structural fault within the moving portion of the object in response to the generated signal.

2. A method for nondestructively inspecting an elongated magnetically permeable object as defined in claim 1, wherein the step of changing the induced static magnetic flux is accomplished by increasing the static magnetic flux.

3. A method for nondestructively inspecting an elongated magnetically permeable object as defined in claim 2, wherein the increasing of the static magnetic flux is accomplished by means of at least one auxiliary pole which has the same magnetic poling as the first primary pole.

4. A method for nondestructively inspecting an elongated magnetically permeable object as defined in claim 1, wherein the step of changing the static magnetic flux is accomplished by decreasing the induced static magnetic flux.

5. A method for nondestructively inspecting an elongated magnetically permeable object as defined in claim 4, further including the step of generating another signal in a portion of the object downstream from the first primary pole and upstream from the at least one flux-changing means where combined static and opposing magnetic fluxes magnetically saturate such portion and where the eddy currents generated adjacent to the first primary pole have not decayed such that eddy current changes representative of structural faults can be readily detected; and determining the location and magnitude of a structural fault within the moving portion of the object in response to the generated signals.

6. A method for nondestructively inspecting an elongated magnetically permeable object as defined in claim 4, wherein the decreasing of the induced static magnetic flux is accomplished by means of at least one auxiliary pole which has the same magnetic poling as the second primary pole.

7. A method for nondestructively inspecting an elongated magnetically permeable object as defined in claim 1, further including the steps of:

changing the magnitude of the static magnetic flux at a portion of the object by means of another flux-changing means positioned on the magnet device between the first and second primary poles and downstream of the one flux-changing means where eddy currents induced at the one flux-changing means have decayed and where the object is generally at magnetic saturation, such change in magnitude being in a direction opposite to the change in magnitude adjacent to the one flux-changing means, the changing magnetic flux at the other flux-changing means inducing circumaxial eddy currents and associated opposing magnetic flux in a portion of the object adjacent to the other flux-changing means;

generating another signal in a portion of the object downstream from the other flux-changing means where combined static and opposing magnetic fluxes magnetically saturate such portion and where the eddy currents induced at the other flux-changing means have not decayed such that eddy current changes representative of structural faults can be readily detected; and wherein the step of determining is also in response to the other signal.

8. A method for nondestructively inspecting an elongated magnetically permeable object as defined in claim 7 wherein the one flux-changing means increases the static magnetic flux, and the other flux-changing means decreases the static magnetic flux.

9. A magnetic inspection device for nondestructively detecting structural faults in elongated objects comprising:

magnet means including first and second primary magnetic poles oppositely polarized relative to each other and spaced from one another for positioning and movement longitudinally relative to an elongated magnetically permeable object to be tested, the first primary pole being positioned upstream of the second primary pole relative to magnet means movement, the magnet means further including at least one auxiliary magnetic pole provided on the magnet means between the primary poles, the auxiliary pole having the same poling as one of the primary poles, the primary poles inducing a static magnetic flux through a longitudinal section of an object extending between the primary poles to at least a near-saturation level, the auxiliary pole changing the magnitude of the induced static magnetic flux in a portion of the object adjacent to the auxiliary pole, the primary poles and the auxiliary pole inducing circumaxial eddy currents and associated opposing magnetic fluxes in moving portions of the object adjacent to the first primary pole and the auxiliary pole, the auxiliary pole being located downstream of the first primary pole such that at a portion of the object adjacent to the auxiliary pole, the eddy currents generated by the first primary pole have decayed and such portion of the object is at least at a near-saturation level;

at least one eddy current change detecting means positioned downstream of the auxiliary pole such that the detecting means is to be positioned adjacent to a portion of the object where combined static and opposing magnetic fluxes magnetically saturate such portion and where eddy currents induced by the auxiliary pole have not decayed such that eddy current changes representative of structural faults generate at least one detectable signal in the eddy current change detecting means; and a digital processor responsive to the at least one signal for determining the location and magnitude of a structural fault within the moving portion of the object.

10. A magnetic inspection device as defined in claim 9 wherein the at least one auxiliary pole has the same poling as the first primary pole, the auxiliary pole increasing the static magnetic flux to magnetic saturation.

11. A magnetic inspection device as defined in claim 9 wherein the at least one auxiliary pole has the opposite poling as the first primary pole, the at least one auxiliary pole decreasing the static magnetic flux toward a near-saturation level.

12. A magnetic inspection device as defined in claim 9 further including another eddy current change detecting means positioned downstream of the first primary pole and upstream of the at least one auxiliary pole such that the other detecting means is adjacent to a portion of the object where combined static and opposing magnetic fluxes magnetically saturate such portion and where eddy currents induced by the primary poles have not decayed such that eddy current changes representative of structural faults generate another detectable signal in the other eddy current change detecting means, and wherein the digital processor is responsive to the signals generated by the eddy current change detecting means for determining the location and magnitude of a structural fault within the moving portion of the object.

13. A magnetic inspection device as defined in claim 9 further including:

another auxiliary magnetic pole having the opposite poling as the one auxiliary pole and being positioned between the primary poles and downstream of the one auxiliary pole, the other auxiliary pole changing the magnitude of the static magnetic flux in a portion of the object adjacent to the other auxiliary pole, whereby circumaxial eddy currents and associated opposing magnetic flux are induced at a portion of the object adjacent to the other auxiliary pole, the other auxiliary pole being located downstream of the one auxiliary pole such that at a portion of the object adjacent to the other auxiliary pole the eddy currents generated by the one auxiliary pole have decayed and such portion of the object is at at least a near-saturation level; and another eddy current change detecting means positioned downstream of the other auxiliary pole such that the other detecting means is adjacent to a portion of the object where combined static and opposing magnetic fluxes magnetically saturate such portion and where eddy currents induced by the other auxiliary pole have not decayed such that eddy current changes representative of structural faults generate another detectable signal in the other eddy current change detecting means, and wherein the digital processor is responsive to the signals generated by the eddy current change detecting means for determining the location and magnitude of a structural fault within the moving portion of the object.

14. A magnetic inspection device as defined in claim 13 wherein the one auxiliary pole increases the static magnetic flux, and the other auxiliary pole decreases the static magnetic flux.

15. A magnetic inspection device as defined in claim 9 wherein the magnet means is a permanent magnet.

16. A magnetic inspection device as defined in claim 9 further including at least one primary ferromagnetic member magnetically coupling the primary poles to form a magnetic flux return path.

17. A magnetic inspection device as defined in claim 16 wherein the at least one auxiliary pole is magnetically coupled to the at least one primary ferromagnetic member.

18. A magnetic inspection device as defined in claim 9 further including:

another auxiliary pole positioned downstream of the at least one eddy current change detecting means and upstream of the second primary pole, the one auxiliary pole and the other auxiliary pole having opposite poling relative to each other; and an auxiliary housing mounted within the inspection device between the primary poles, the housing supporting therein the auxiliary poles and the at least one eddy current change detecting means in fixed position relative to each other.

19. A magnetic inspection device as defined in claim 18 wherein the one auxiliary pole has the same poling as the first primary pole.

20. A magnetic inspection device as defined in claim 18 further including an auxiliary ferromagnetic member magnetically coupling the auxiliary poles supported within the auxiliary housing.

21. A magnetic inspection device as defined in claim 18 further including at least one link member for pivotally coupling the auxiliary housing to the at least one primary ferromagnetic member for adjusting the position of the housing within the magnet means.

22. A magnetic inspection device as defined in claim 18 wherein the one and the other auxiliary poles are respectively first and second auxiliary poles constituting a first set of auxiliary poles, the inspection device further including a second set of oppositely poled third and fourth auxiliary poles positioned downstream of the first set, the first and second auxiliary poles of the first set having opposite poling relative to respective third and fourth auxiliary poles of the second set, and a second eddy current change detecting means positioned between the third auxiliary and fourth auxiliary poles of the second set.

23. A magnetic inspection device as defined in claim 22 wherein the first auxiliary pole has the same poling as the first primary pole.

24. A magnetic inspection device for nondestructively detecting structural faults in elongated objects comprising:

magnet means including first and second primary magnetic poles oppositely poled relative to each other and spaced from one another for positioning and movement longitudinally relative to an elongated magnetically permeable object to be tested, the first primary pole being positioned upstream of the second primary pole relative to magnet means movement, the magnet means further including at least one auxiliary pole positioned on the magnet means between the primary poles, the auxiliary pole having the same poling as the second primary pole, the primary poles inducing a static magnetic flux through a longitudinal section of an object extending between the primary poles for placing the object in magnetic saturation, the at least one auxiliary pole decreasing the magnitude of the static magnetic flux in a portion of the object adjacent to the auxiliary pole, the primary poles and the auxiliary pole inducing circumaxial eddy currents and associated opposing magnetic fluxes in moving portions of the object adjacent to the first primary pole and the auxiliary pole, the auxiliary pole being located downstream of the first primary pole such that at a portion of the object adjacent to the auxiliary pole the eddy currents generated by the first primary pole have decayed and such portion of the object is in magnetic saturation;

a first eddy current change detecting means positioned downstream from the at least one auxiliary pole such that the first detecting means is to be positioned adjacent to a portion of the object where combined static and opposing magnetic fluxes magnetically saturate such portion and where eddy currents induced by the at least one auxiliary pole have not decayed such that eddy current changes representative of structural faults generate a first detectable signal in the first eddy current change detecting means;

a second eddy current change detecting means positioned downstream of the first primary pole and upstream of the at least one auxiliary pole, the second detecting means to be positioned adjacent to a portion of the object where combined static and opposing magnetic fluxes magnetically saturate such portion and where eddy currents induced by the first primary pole have not decayed such that eddy current changes representative of structural faults generate a second detectable signal in the second eddy current change detecting means; and a digital processor responsive to the first and second signals for determining the location and magnitude of a structural fault within the moving portion of the object to be tested.

25. A magnetic inspection device as defined in claim 24 wherein the magnet means further includes another auxiliary pole positioned downstream of the first primary pole and upstream of the second eddy current change detecting means, the other auxiliary pole having the same poling as the first primary pole such that the other auxiliary pole increases the magnitude of the static magnetic flux in a portion of the object adjacent to the auxiliary pole such that circumaxial eddy currents are induced in such adjacent portion, the second eddy current change detecting to be positioned adjacent a portion of the object where the object is magnetically saturated and eddy currents induced by the other auxiliary pole have not decayed, whereby eddy current changes representative of structural faults are detected.

26. A magnetic inspection device as defined in claim 24 wherein the magnet means is a permanent magnet.

* * * * *

UNITED STATES PATENT AND TRADEMARK OFFICE
CERTIFICATE OF CORRECTION

PATENT NO.   : 5,751,144
DATED        : May 12, 1998
INVENTOR(S)  : Herbert R. Weischedel It is certified that error appears in the above-indentified patent and that said Letters Patent is hereby corrected as shown below:

```
     Column 5, line 23, delete "FIG. 1a" and substitute
--FIG. 1b--.
     Column 6, line 22, delete "an" and substitute --a--.
     Column 8, line 26, delete "A" and substitute --a--.
     Column 9, line 34, delete "an" and substitute --a--;
line 66, delete "an" and substitute --a--.
     Column 12, line 15, delete "an" and substitute --a--.
     Column 13, line 12, delete "62,62" and substitute --62, 64--;
line 53, after "1" insert --a--.
     Column 14, line 15, delete "an" and substitute --a--;
line 59, after "fully" insert --described--.
     Column 16, line 36, delete "an" and substitute --a--;
line 60, delete "an" and substitute --a--.
```

Signed and Sealed this

Fourth Day of May, 1999

Attest:

*Attesting Officer*

Q. TODD DICKINSON

*Acting Commissioner of Patents and Trademarks*